United States Patent [19]
Jorgensen

[11] Patent Number: 5,439,473
[45] Date of Patent: Aug. 8, 1995

[54] SAFETY LANCET

[75] Inventor: Peter Jorgensen, Helsinge, Denmark

[73] Assignee: Modulohm A/S, Herlev, Denmark

[21] Appl. No.: 166,450

[22] Filed: Dec. 13, 1993

[51] Int. Cl.⁶ .............................................. A61B 17/34
[52] U.S. Cl. ..................................... 606/182; 604/136
[58] Field of Search ....................... 606/181, 182, 183; 604/136, 157

[56] References Cited

U.S. PATENT DOCUMENTS

| | | | |
|---|---|---|---|
| 4,442,836 | 4/1984 | Meinecke et al. | 606/182 |
| 4,449,529 | 5/1984 | Burns et al. | 606/182 |
| 4,469,110 | 9/1984 | Slama | 606/182 |
| 4,539,988 | 9/1985 | Shirley et al. | |
| 4,553,541 | 11/1985 | Burns | 606/182 |
| 4,677,979 | 7/1987 | Burna | 606/181 |
| 4,869,249 | 9/1989 | Crossman et al. | |
| 4,976,724 | 12/1990 | Nietro et al. | 606/181 |
| 4,983,178 | 1/1991 | Schnell | |
| 4,994,068 | 2/1991 | Hufnagle | |
| 5,026,388 | 6/1991 | Ingalz | 606/182 |
| 5,070,886 | 12/1991 | Mitchen et al. | |
| 5,100,427 | 3/1992 | Crossman | 606/182 |
| 5,120,311 | 6/1992 | Sagstetter et al. | |

FOREIGN PATENT DOCUMENTS

| | | |
|---|---|---|
| 0036443 | 9/1981 | European Pat. Off. |
| 0081665 | 4/1986 | European Pat. Off. |
| 0204892 | 12/1986 | European Pat. Off. |
| 0178384 | 6/1991 | European Pat. Off. |
| 0199484 | 3/1993 | European Pat. Off. |
| 2508305 | 12/1982 | France |
| 85/04089 | 9/1985 | WIPO |
| 93/00044 | 1/1993 | WIPO |

Primary Examiner—Peter A. Aschenbrenner
Assistant Examiner—Nancy Mulcare
Attorney, Agent, or Firm—Merchant & Gould, Smith, Edell, Welter & Schmidt

[57] ABSTRACT

A lancet assembly for pricking a person's skin for the purpose of causing a drop of blood to seep out, which can be collected and analyzed. The lance assembly comprises a housing and spring means carrying a lancet blade in the housing. The spring means has a non-linear characteristics, so that when the spring means is released from a compressed state a first spring constant is effective during an initial expansion of the spring means up to a predetermined limit of expansion, and a second spring constant smaller than the first spring constant is effective during a further expansion of the spring means beyond the predetermined limit of expansion.

3 Claims, 2 Drawing Sheets

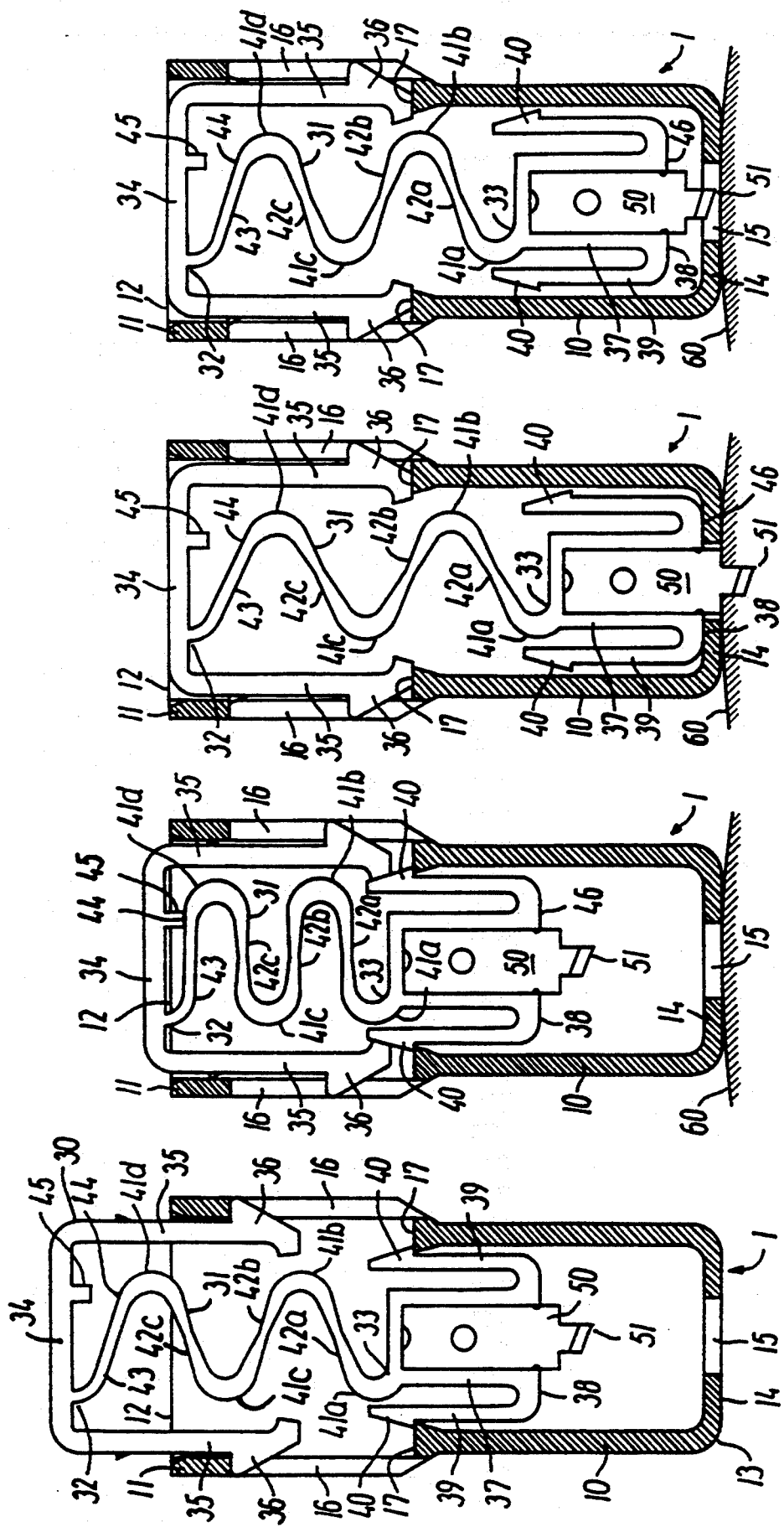

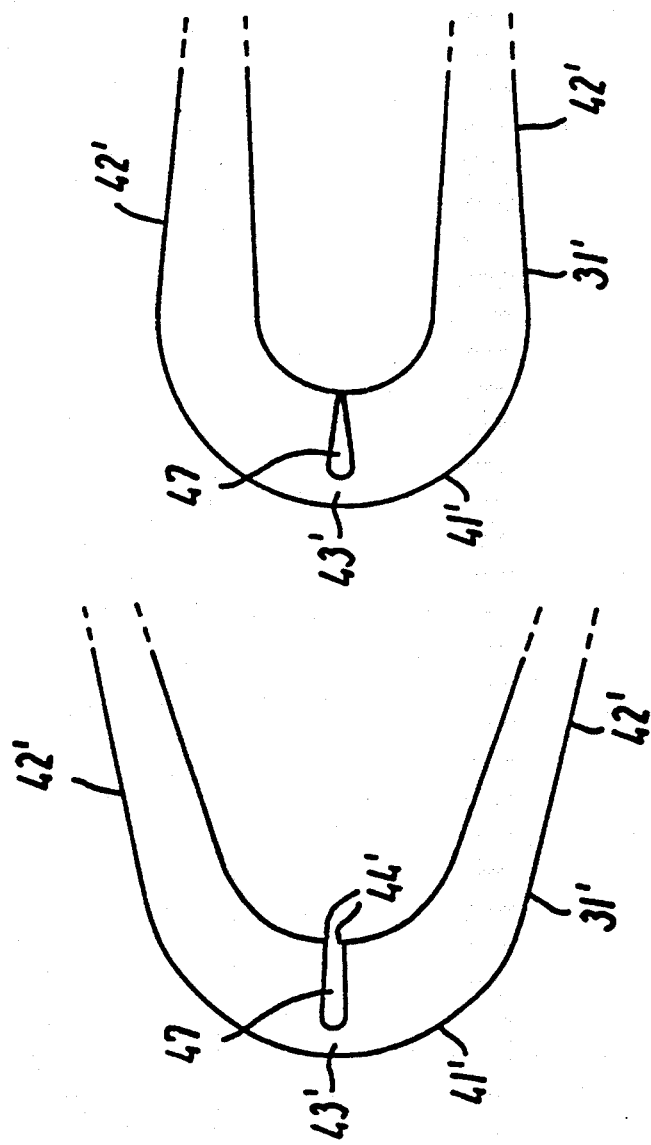

SAFETY LANCET

FIELD OF THE INVENTION

The invention concerns a safety lancet which is used for taking very small blood samples from a person. Such a safety lancet has a sharp tip or a lancet blade which is briefly thrust out of a lancet housing and cuts or pricks a small hole in the person's skin, whereby a small amount of blood, e.g. a drop, seeps out and can be collected and analyzed with equipment, which is not part of this invention.

BACKGROUND OF THE INVENTION

Because of the ever increasing interest in avoiding infection a plurality of disposable safety lancets have been developed, it being ensured with various means that the safety lancet can only be used a single time. Further, there are safety lancets in which the lancet blade only briefly protrudes from an opening in the lancet housing and is immediately retracted again, so that the user and others cannot get into contact with the lancet blade, which has touched the person's blood and can therefore be a potential disease carrier.

Safety lancets of the present type comprises a spring which is compressed and then released. The spring then drives the lancet blade at a great rate inside the lancet housing toward the opening, and owing to the kinetic energy achieved by the spring and the lancet blade the spring extends beyond its equilibrium so that the lancet blade briefly protrudes from the opening. The spring then retracts to its relaxed position in which the lancet blade is retracted from the opening. It is here necessary that the spring is capable of imparting a high rate and thus much kinetic energy to the lancet blade, and a relatively stiff spring is required for this purpose. However, stiff springs tend not to permit any great movement of the free end of the spring with the lancet blade beyond the equilibrium of the spring, and the distance between the maximally extended position of the lancet blade and the retracted position can therefore frequently be so short that the lancet blade when retracted is in an inexpediently advanced position, so that it will be possible to touch the lancet blade with the consequent risk of transmission of infection.

It is therefore desirable that the spring has a long travel beyond its relaxed position following release, enabling a great distance between the maximally extended position of the lancet blade and its retracted position.

SUMMARY OF THE INVENTION

The invention provides a safety lancet having a specially constructed spring which has a nonlinear characteristic, i.e. the relation between the deformation of the spring and the force required for this. When the safety lancet of the invention is loaded, the spring has deformed maximally, and in the maximally deformed state the spring has a relatively great spring constant, i.e. the spring is stiff and thus has a high content of energy. When the safety lancet is released, the mechanical energy contained in the spring is released, and the lancet blade at one end of the spring is thrust out at a great rate. This rate is greatest at the moment when the spring reaches its relaxed equilibrium, and when the spring has a relatively small spring constant, said spring being now a "soft" spring, and the lancet blade therefore obtains a relatively long movement past the equilibrium of the spring before the lancet blade is retracted again.

BRIEF DESCRIPTION OF THE DRAWINGS

FIG. 1 shows a longitudinal section through a safety lancet according to the invention in a starting position, FIG. 2 shows the safety lancet of FIG. 1 with the spring compressed, FIG. 3 shows the safety lancet of FIGS. 1-2 with the lancet blade protruding from the lancet housing, FIG. 4 shows the safety lancet of FIGS. 1-3 after use, FIG. 5 shows a detail of a spring in an alternative embodiment of the invention in a relaxed state, FIG. 6 shows the same detail as FIG. 5, but in a compressed state.

DESCRIPTION OF THE PREFERRED EMBODIMENTS

FIGS. 1-4 show a safety lancet 1 according to the invention. The safety lancet 1 has an elongate lancet housing 10, which is shown in longitudinal section in FIGS. 1-4. Upwardly in the drawings the lancet housing 10 has a first end 11 with a first opening 12 and downwardly in the drawings a second end 13 which is terminated with a plate 14 having a second opening 15.

The interior of the lancet housing 10 accommodates a movable part 30, which is movable longitudinally of the elongate lancet housing 10. The movable part 30 comprises a Z-folded part 31 having a first end 32 and a second end 33. The first end 32 of this Z-folded part 31 is integral with a transverse part 34 having an elongate arm 35 at each of its two ends. At their free ends the elongate arms 35 have a protruding hook 36 each, which is positioned in elongate openings 16 in opposed side walls of the lancet housing 10.

The second end 33 of the Z-folded part 31 is integral with a block 37, to which a lancet blade 50 having a sharp tip or edge 51 is secured. The lower end 38 of the block 37 carries two arms 39 which have a protruding hook 40 of triangular shape at their respective free ends.

In the preferred embodiment the entire movable part 30 consists of a plastics material having good resilient properties, e.g. POM, and is molded in one piece.

The Z-folded part 31 serves as a compression spring which has four substantially arc-shaped knees 41a, 41b, 41c and 41d from its second end 33. Between the knees 41a–d the spring has three identical and substantially rectilinear portions 42a, 42b and 42c. The rectilinear portions are thinnest in the center and here have a thickness which is essentially equal to half the thickness in the center of the knees 41a–d, and the thickness varies linearly between the centers of the knees 41a–d and the centers of the rectilinear portions 42a–c. This results in a uniform deformation of this part of the spring by compression. The spring part extending from the second end 33 and comprising the knees 41a–d and the rectilinear portions 42a–c constitutes a first spring section.

Between the first end 32 of the spring and the knee 41d the Z-folded spring 31 has a second spring section 43 of substantially constant thickness. It is noted in particular that near the first end 32 the second spring section 43 has a smaller thickness than the knees 41a–d.

FIG. 1 shows the safety lancet 1 of the invention as delivered to the user ready for use. When the safety lancet 1 is to be used, it is positioned, as shown in FIG. 2, with the plate 14 at its second end 13 engaged with a person's skin 60, and the user then applies a finger pressure to the transverse part 34 which protrudes from the opening 12 at the first end 11 of the lancet housing. The hooks 40 on the arms 39 are engaged with lower edges 17 of the elongate openings 16, thereby temporarily retaining the block 37 with the lancet blade 50 and the second end 33 of the Z-folded spring 31. Pressure on the transverse part 34 causes said part with the arms 34 and the hooks 36 to be moved into the opening 12 in the lancet housing 10, and the spring 31 to be compressed. Because of the geometrical design of the spring its first spring section 41a–d, 42a–c forms a relatively stiff spring section, and its second spring section 43 forms a relatively soft spring section. Thus, the first spring section has a first spring constant which is greater than a second spring constant of the second spring section. The spring constant of a spring is defined as the ratio of the applied force to the resulting spring deformation.

When the transverse part 34 with the arms 35 is pressed into the lancet housing, the second spring section 43 will be deformed more than the first spring section 41a–d, 42a–c because of the smaller spring constant. The second spring section 43 has an engagement face 44 opposite the first end 32 and at the transition to the knee 41d. Before the entire spring 31 has been fully compressed, the second spring section 43 will be deformed so much that the engagement face 44 contacts the end of a pin 45, thereby preventing further compression of the second spring section 43. Upon further compression to the position shown in FIG. 2, only the first spring section 41a–d, 42a–c of the spring will be compressed. The first section and the second section of the spring are interconnected in series, and after the second spring section 43 has been fully compressed with the engagement face 44 engaged with the pin 45, only the first spring section is compressed, and in the further compression the spring is therefore stiffer than in the first compression phase.

FIG. 2 shows the spring 31 in its almost completely compressed position immediately prior to release. The free ends of the arms 35 touch the hooks 40 on the arms 39 in FIG. 2. Then the transverse part 34 is pressed additionally into the lancet housing 10, whereby the free ends of the arms 35 press the hooks 40 against each other so that they are disengaged from the lower edges 17 of the openings 16, and the free ends of the arms 35 engage the lower edges 17. The spring is then free to expand, and the stiff, first spring section 41a–d, 42a–c expands, while the second spring section 43 is still compressed and the engagement face 44 is engaged with the end of the pin 45. During this first expansion the spring drives the block 37 with the lancet blade 50 at a great rate against the second end 13 of the lancet housing 10, and en route also the second spring section 43 expands, and the engagement face 44 disengages the pin 45.

FIG. 3 shows the safety lancet in a position in which the spring 31 with its first section and second section is expanded maximally, and in which the sharp edge 51 of the lancet blade 50 has pricked a hole in the person's skin 60. The underside 46 of the block 37 engages the inner side of the plate 14 in FIG. 3, and it will be seen that the insertion depth of the tip 51 of the lancet blade is equal to the length with which the top 51 protrudes from the underside 46 of the block 37 less the thickness of the plate 14. The second opening 15 in the plate 14 is here a narrow rectangular opening which matches the shape of the lancet blade 50. The engagement pressure with which the lancet housing is pressed against the person's skin 60 is hereby prevented from influencing the insertion-depth, since the skin 60 cannot be pushed significantly into the narrow second opening 15. Thus, the insertion depth is always well-defined.

The block 37 with the lancet blade 50 and the arms 39 together with part of the first spring section have a certain mass which obtains some kinetic energy after release. This kinetic energy causes the spring, and in particular the soft second spring section 43, to expand beyond the equilibrium to the position shown in FIG. 3.

FIG. 4 shows the safety lancet 1, where the spring 31 has assumed its state of equilibrium again after use, and where in particular the soft second spring section 43 has pulled the rest of the spring with the block 37 and the lancet blade 50 back from the maximally expanded position in FIG. 3. The tip 51 of the lancet blade is here retracted after insertion into the person's skin 60 and is present in the second opening 15 safely spaced from the outer side of the plate 14, such that any contact with the tip 51 is excluded.

The kinetic energy to move the block 37 with the lancet blade is created substantially by the stiff first spring section 41a–d, 42a–c, while the soft second spring section 43 essentially permits a long travel of the lancet blade beyond the equilibrium of the spring and moreover retracts the lancet blade from its extended position.

FIGS. 5 and 6 show a section of a spring 31' having a knee 41' and two rectilinear spring portions 42'. Like in FIGS. 1–4, the knee 41' here has twice the thickness of the centers of the rectilinear portions 42'. A notch 47 is provided centrally on the knee 41' on the inner side thereof, said knee 41' having a part 43' of considerably smaller thickness than the rest of the knee at the bottom of the notch 47. In FIG. 5 the knee 41' is shown in its state of equilibrium corresponding to FIGS. 1 and 4, and FIG. 6 shows the knee in its compressed position corresponding to FIG. 2. The reduced thickness at the bottom of the notch 47 results in a soft spring section 43' having a smaller spring constant than the rest of the knee 41' and the rectilinear portions 42'. Initial compression of the spring therefore causes compression of preferably the spring section 43', and the opposed edges 44' at the free end of the notch 47 to approach each other, and when the edges 44' meet, the soft spring section 43' cannot be compressed further. In case of compression of the spring 31' beyond this limit, the spring will therefore have a greater spring constant and thus appear as a stiffer spring than during the initial compression. However, the embodiment in FIGS. 5 and 6 requires great precision in the making of the notch 47 to obtain precisely the desired effect.

The Z-folded part 31 may be formed with another ratio of the length of the rectilinear portions 42a–c to the radius of curvature of the knees 41a–d, e.g. so that it will be S-shaped or wave-shaped.

The entire movable part 30 lends itself to mass-production by injection molding in a simple two-part mold.

In another alternative embodiment, which is not shown in the drawings, the complete spring consists of two springs arranged in parallel, one spring being firmly connected to the transverse part 34 and the block 37, and a further spring being connected only with the block 37 and having a free end which faces the transverse part 34, which it contacts only upon compression beyond a certain limit.

What is claimed is:

1. A lancet assembly comprising:
   a. a housing;

b. a spring at least partially within the housing, the spring being movable between a compressed position and an expanded position, the spring including a first end and a second end, the first end including a blade the spring additionally including a first section, and a second section;

c. means for restricting compression of the second section to a predetermined limit of compression;

d. means for retaining the blade within the housing when the spring is moved to the compressed position; and e. means for releasing the spring from the compressed position, the releasing means acting in cooperation with the blade retaining means, whereby when the spring is released and moved into the expanded position, the blade protrudes from the housing, piercing the skin.

2. The lancet assembly of claim 1, wherein the compression restricting means of the second section further comprises engagement portions adapted to mutually engage when the second section is compressed to the predetermined limit of compression, so as to restrict the compression thereof, and adapted to disengage when the spring expands beyond a predetermined limit of expansion.

3. The lancet assembly of claim 2, wherein the spring comprises a notch for locally weakening the spring, the notch adapted to be narrowed during compression of the spring, adapted to close when the spring is compressed to a predetermined limit of compression, and adapted to open when the spring is expanded beyond the predetermined limit of expansion.

* * * * *